United States Patent
Mansour et al.

(10) Patent No.: US 7,753,902 B1
(45) Date of Patent: Jul. 13, 2010

(54) METHODS AND DEVICES FOR TISSUE MONITORING

(76) Inventors: Hebah Noshy Mansour, 14759 Hardaway Dr., La Mirada, CA (US) 90638; Ramez Emile Necola Shehada, 14759 Hardaway Dr., La Mirada, CA (US) 90638

( * ) Notice: Subject to any disclaimer, the term of this patent is extended or adjusted under 35 U.S.C. 154(b) by 0 days.

(21) Appl. No.: 11/561,362

(22) Filed: Nov. 17, 2006

Related U.S. Application Data

(60) Provisional application No. 60/738,011, filed on Nov. 17, 2005.

(51) Int. Cl.
*A61M 27/00* (2006.01)
*A61M 1/00* (2006.01)
*A61B 5/00* (2006.01)
*A61B 6/00* (2006.01)

(52) U.S. Cl. .......... 604/541; 604/540; 604/546; 604/523; 600/323; 600/322; 600/324; 600/325; 600/327; 600/328; 600/310; 600/473; 600/478

(58) Field of Classification Search .......... 604/540, 604/541, 546, 523; 600/562, 573, 575, 578, 600/581, 31, 309, 323, 322, 324, 325, 310, 600/473, 476, 478, 479, 623, 500–504, 507
See application file for complete search history.

(56) References Cited

U.S. PATENT DOCUMENTS

| | | | |
|---|---|---|---|
| 3,674,013 A * | 7/1972 | Polanyi | 600/325 |
| 4,248,214 A * | 2/1981 | Hannah et al. | 604/523 |
| 4,329,994 A * | 5/1982 | Cooper | 604/98.01 |
| 4,523,920 A * | 6/1985 | Russo | 604/266 |
| 4,537,197 A * | 8/1985 | Hulka | 600/338 |
| 4,782,819 A * | 11/1988 | Adair | 600/109 |
| 4,938,218 A * | 7/1990 | Goodman et al. | 600/338 |
| 5,020,537 A * | 6/1991 | Gunther | 600/311 |
| 5,108,364 A * | 4/1992 | Takezawa et al. | 604/43 |
| 5,193,542 A * | 3/1993 | Missanelli et al. | 600/338 |
| 5,271,410 A * | 12/1993 | Wolzinger et al. | 600/505 |
| 5,291,896 A * | 3/1994 | Fonger et al. | 600/526 |
| 5,514,092 A * | 5/1996 | Forman et al. | 604/101.03 |
| 5,531,679 A * | 7/1996 | Schulman et al. | 604/65 |
| 5,775,328 A * | 7/1998 | Lowe et al. | 600/458 |
| 6,106,475 A * | 8/2000 | Lowe et al. | 600/462 |
| 6,210,346 B1 * | 4/2001 | Hall et al. | 600/561 |
| 6,231,514 B1 * | 5/2001 | Lowe et al. | 600/462 |
| 6,517,477 B1 * | 2/2003 | Wendlandt | 600/114 |
| 6,524,261 B2 * | 2/2003 | Talish et al. | 601/2 |
| 6,716,176 B1 * | 4/2004 | Weston et al. | 600/462 |
| 6,856,821 B2 * | 2/2005 | Johnson | 600/345 |
| 2002/0107478 A1 * | 8/2002 | Wendlandt | 604/95.01 |
| 2003/0060680 A1 * | 3/2003 | Wendlandt | 600/114 |

(Continued)

*Primary Examiner*—Leslie R Deak
*Assistant Examiner*—Adam Marcetich

(57) ABSTRACT

The present invention is directed to a system and method for monitoring the physiological parameters of an organ or tissue during and after surgery. The system has a probe and a monitoring unit. In one embodiment the probe includes features for convenient, fixed and releasable attachment to surgical drains without interfering with their normal fluid-draining function while utilizing their suction to enhance the probe-to-tissue interface for improved sensing. An applicator is provided to facilitate such attachment. The monitoring unit which controls the sensors of the probe includes a processor to process, record and display the sensor data. This system may be valuable for monitoring transplanted organs and tissue grafts during the critical postoperative period when most of the clinical complications, such as vascular thrombosis, may occur.

12 Claims, 10 Drawing Sheets

U.S. PATENT DOCUMENTS

2004/0249360 A1* 12/2004 Spehalski .................. 604/523
2004/0260249 A1* 12/2004 Kulessa ..................... 604/256
2006/0178571 A1* 8/2006 Barnett ..................... 600/311

* cited by examiner

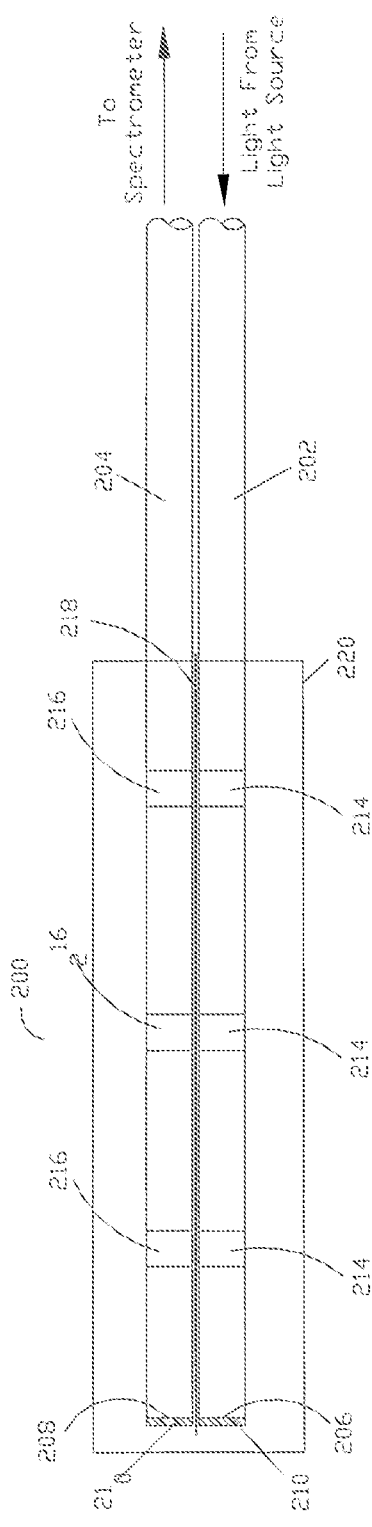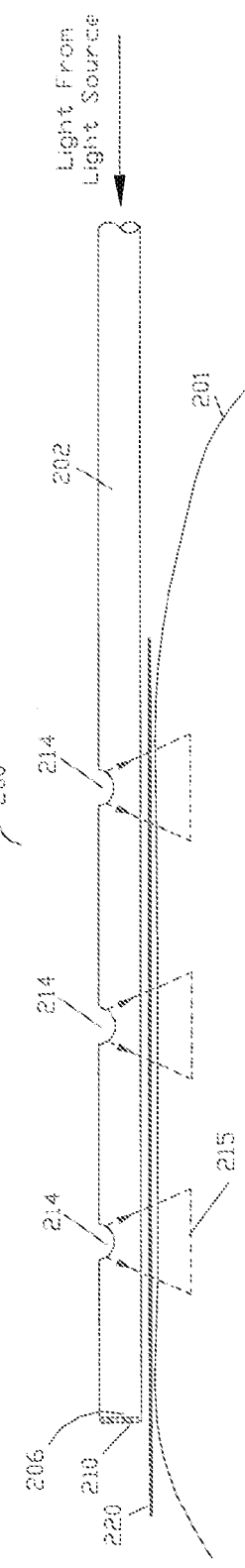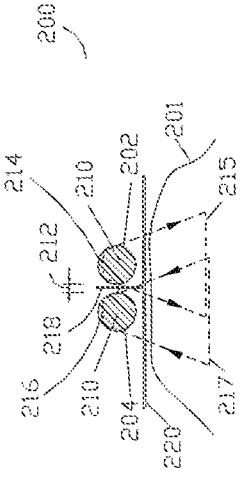
FIG. 6A
FIG. 6B
FIG. 6C

METHODS AND DEVICES FOR TISSUE MONITORING

CROSS-REFERENCE TO RELATED APPLICATION(S)

This Application claims the benefit of U.S. Provisional Application No. 60/738,011, filed Nov. 17, 2005, entitled Methods and Probes for Tissue Monitoring, the entire contents of which are incorporated herein by reference.

FIELD OF THE INVENTION

The present invention relates to a system and method for monitoring tissue during and after surgery, in particular, a system and method utilizing an attachable probe that adheres to surgical drains for enhanced interfacing with the tissue.

BACKGROUND OF THE INVENTION

Vascular complications may occur after organ transplantation which can compromise the survival of the organ and, in some cases, the patient. Surgical resection of some organs such as the liver may introduce vascular complications to the remaining portion of the organ depending on the type and extent of the resection. This makes it important to monitor the surgically affected organs during the postsurgical period for the early detection of complications which may enable organ-saving intervention before the occurrence of irreversible tissue damage or total organ loss.

For example, monitoring of hepatic oxygenation is essential after liver transplantation and resection. Currently, the measurement of the liver enzymes and clotting factors via blood analysis is the only reliable way to monitor liver dysfunction. Changes in these laboratory values can be detected only after significant liver damage has already occurred and hence intervention usually takes place retrospectively. Also, these tests have no dynamic value since they indicate the liver condition only at the time when the blood sample is withdrawn.

Current organ monitoring technology offers probes that may require stitching or gluing to the tissue and therefore may not be easy to apply or remove especially if used inside the body, which has been a key limitation to wide acceptance in the medical field. Probe stitching to the surface of an organ may also disturb the local microvasculature, cause subcapsular hematoma, and interfere with the measurement of the probe. Following are some examples of commercially available organ and tissue monitoring technologies.

Thermodilution organ monitoring technology such as that produced by Hemedex Inc., MA, uses a catheter-like probe that is inserted into the organ to measure its perfusion using thermodilution. The tip of the catheter-like probe includes a thermistor that is heated to remain slightly above the tissue temperature. The local perfusion is estimated from the power used in heating the thermistor, which generally depends on the ability of the tissue to dissipate heat by both thermal conduction within the tissue and by thermal convection due to tissue blood flow. This organ-invasive probe may cause bleeding, subcapsular hematoma, and may require extra care during insertion to avoid the puncture of underlying vessels.

Doppler ultrasound graft monitoring technology such as that produced by Cook Vascular Inc., PA, uses a suturable cuff probe that is fitted around the vessels supplying the tissue to assess its blood flow using Doppler ultrasound. Post-monitoring, the cuff probe may be difficult to remove and may left permanently around the vessel.

Optical tissue monitoring technology such as that produced by Spectros Corporation, CA, uses button-like probes are stitched to the tissue to measure its oxygen saturation using reflectance spectroscopy (e.g. Stitching can complicate probe application and removal. Also, stitching may disturb the local microcirculation and introduces measurement errors.

Laser Doppler Flowmetry tissue monitoring technology such as that produced by Perimed A B, Sweden, uses button-like probes are stitched to the tissue to measure its blood perfusion using laser Doppler flowmetry. Again, stitching can complicate probe application and removal and disturb the local microcirculation thereby introducing measurement errors.

US Publication No. US 2004/0230118A1 with publication date Nov. 18, 2004 discloses a Jackson-Pratt (JP) surgical drain with embedded sensors for monitoring organs and tissues. One disadvantage of this configuration is the inability of the user to select the location of the sensors along the length of the drain. In addition, this configuration is constrained to a specific category of surgical drains having a shape and cross-section that can accommodate embedded sensors.

Surgical drains (or surgical wound drains, used interchangeably herein) are routinely used in and after many surgical procedures to drain the wound exudate out of the body. Some well-known examples of the surgical drains are the Jackson-Pratt (JP) drains (e.g. Jackson F E and Fleming P M, "Jackson-Pratt brain drain: use in general surgical conditions requiring drainage," International Surgery, Vol. 57, No 8, page 658-659, 1972), and the flat drains (e.g. U.S. Pat. No. 4,317,452 and U.S. Pat. No. 4,257,422), and the Blake drains (e.g. U.S. Pat. Des. 288,962, U.S. Pat. No. 4,398,910, and U.S. Pat. No. 4,465,481). Surgical drains are generally used with a vacuum source to remove wound exudate postoperatively.

SUMMARY OF THE INVENTION

The present invention discloses a method and system for monitoring tissue (or organs, used interchangeably herein) utilizing a versatile probe that may be mounted on various types of surgical drains for the seamless integration into surgical procedures. The system is comprised of a probe and a monitoring unit. The probe may include sensors to measure the physiological parameters of the tissue, a means to adhere to a surgical drain, and through openings that couples to the openings of the surgical drain to allow the passage and drainage of the local wound fluids.

The application and removal of the disclosed probe may not require any additional effort, training or skills beyond that required for the routine application and removal of surgical drains. The probe does not need to be stitched or glued to the tissue as the normal suction of the drain creates local vacuum that brings the probe and the adjacent tissue together thereby holding the probe in position and maintaining good contact between its sensors and the tissue. Furthermore, the sensors of the probe maintain good contact with the tissue because the normal suction of the drain clears the wound fluids that may otherwise isolate the sensors from the tissue and impede their measurement. Moreover, the probe is of a design such that it can be manufactured with greater ease.

Depending on the intended application, the probe may include sensors to measure tissue oxygenation (e.g. percent oxygen saturation, oxygen partial pressure, etc.), perfusion, temperature, pressure, pH, water content, and/or the concentration of biological material (e.g. bile, hemoglobin, etc.) or exogenous materials (e.g. drugs, cytotoxins, etc.). For example, percent oxygen saturation (SaO2) may be the preferred physiological parameter for monitoring transplanted organs and tissue grafts which are susceptible to thrombosis in their newly connected vessels. The monitoring unit which controls the sensors of the probe may include a processor to process, record and display the sensor data.

In one embodiment, the openings of the probe may be holes that are arranged to hydraulically couple to the holes of one surgical drain type. In another embodiment, the openings of the probe may be elongated slots that are arranged to hydraulically couple to the grooves of another surgical drain type.

The monitoring unit which controls the sensors of the probe may include a processor to process, record and display the sensor data.

In one method, the probe may be attached to a surgical drain, both implanted in the body next to the tissue to be monitored, and the probe anchored at the desired position by the vacuum-induced compression of the surrounding tissues created by the normal suction action of the surgical drain.

BRIEF DESCRIPTION OF THE DRAWINGS

FIG. 6A is a bottom view of the line sensor of FIG. 5.

FIG. 6B is a side view of the line sensor of FIG. 5.

FIG. 6C is a front view of the line sensor of FIG. 5.

DETAILED DESCRIPTION OF THE INVENTION

Figure 1:
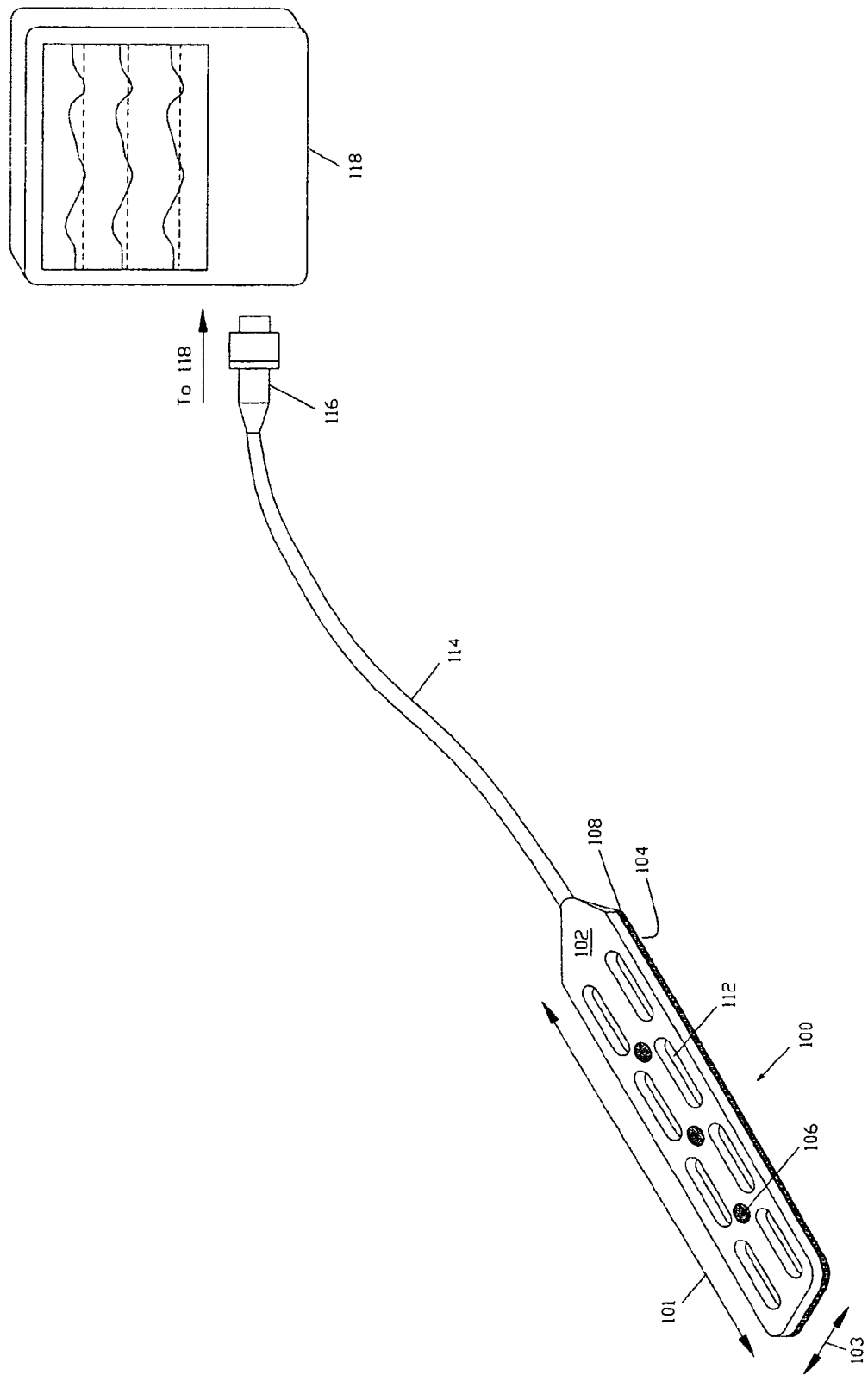
FIG. 1 shows an embodiment of a probe and a monitoring unit in accordance with the present invention.
Figure 2A:
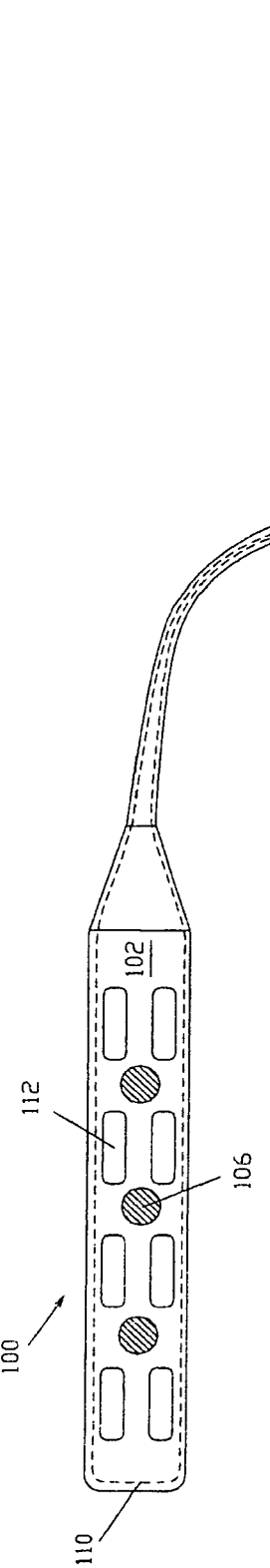
FIG. 2A shows a top view of the probe of FIG. 1.
Figure 2B:
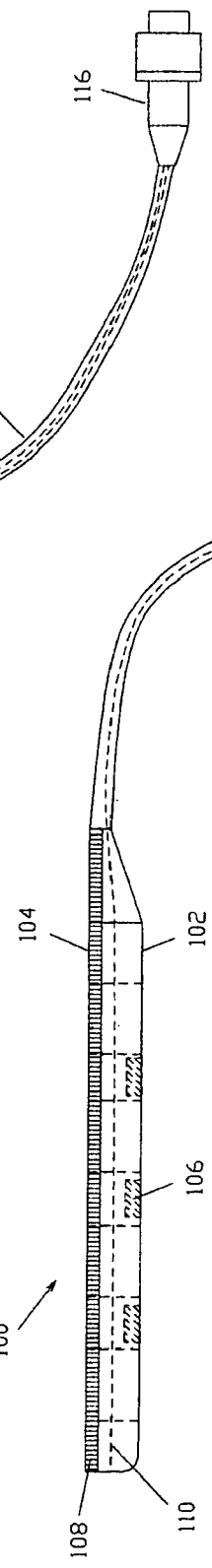
FIG. 2B shows a side view of the probe of FIG. 1.
Figure 2C:
FIG. 2C shows a front view of the probe of FIG. 1.

A preferred embodiment of a probe 100 of the present invention is shown in FIG. 1 and FIG. 2. The illustrated embodiment of the probe 100 is generally elongated, flat and rectangular in shape. A typical probe length 101 may range between 1 to 6 cm and a typical width 103 may range between 5 to 15 mm. The probe may be made of flexible material such as medical grade silicone and may be reinforced by an embedded fiber mesh (not shown) to enhance its structural integrity. For in-vivo applications, the probe may be preferably made of a radiopaque material such as barium-loaded silicone.

The probe 100 may have a probe body with a first surface 102 and a second surface 104. The first surface 102 may include one or more sensors 106 for measuring one or more physiological parameters of an adjacent tissue or organ. Depending on the intended application, the probe may include sensors to measure tissue oxygenation (e.g. percent oxygen saturation, oxygen partial pressure, etc.), perfusion, temperature, pressure, pH, water content, and/or the concentration of biological material (e.g. bile, hemoglobin, etc.) or exogenous materials (e.g. drugs, cytotoxins, etc.).

Figure 3A:
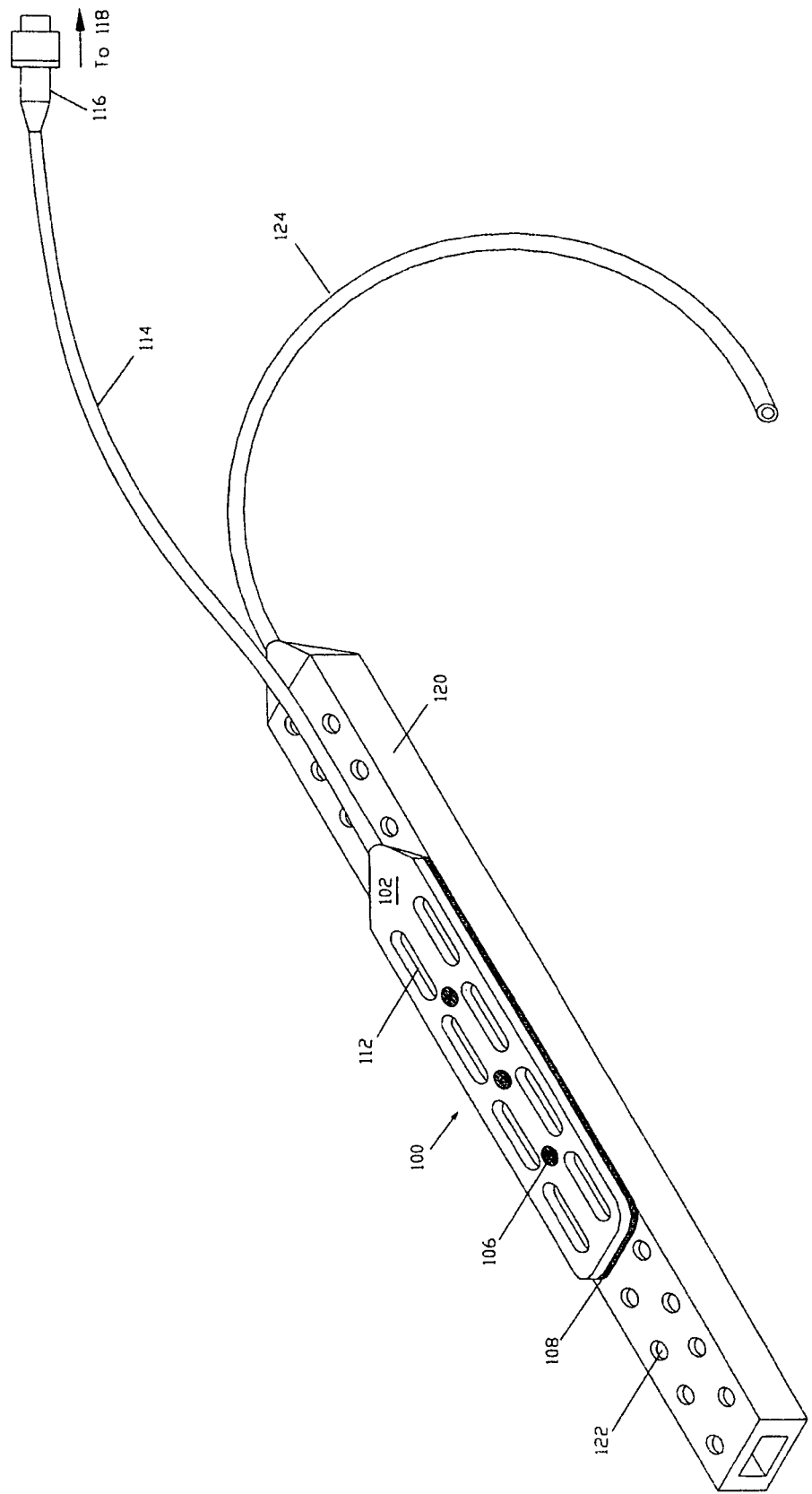
FIG. 3A shows an embodiment of a probe mounted on a surgical drain with draining holes.
Figure 3B:
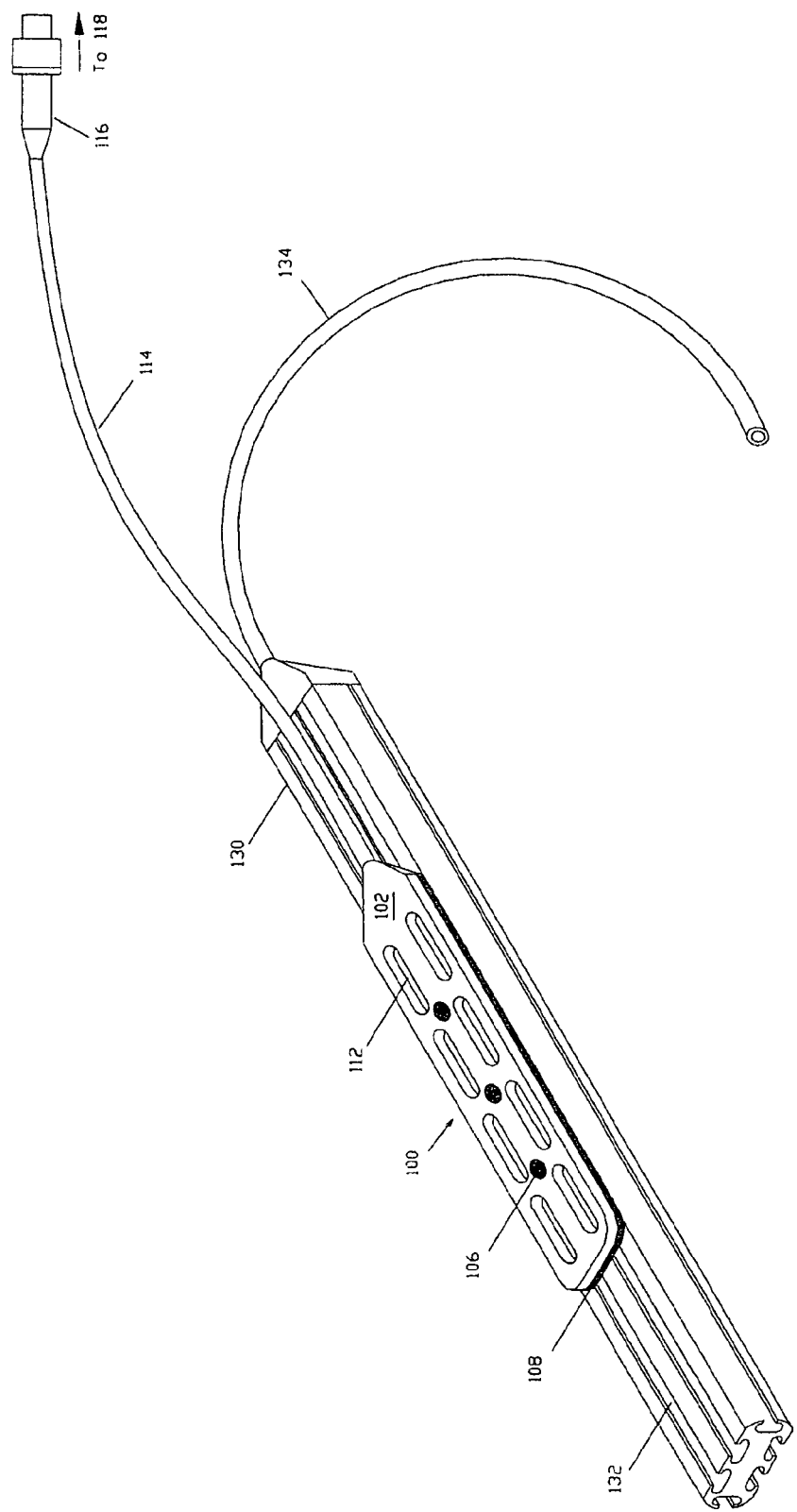
FIG. 3B shows an embodiment of the probe mounted on a surgical drain with draining grooves.

The second surface 104 of the probe may have an adhesive 108 to facilitate the attachment of the probe 100 to surfaces, instruments or devices such as a surgical drain 120 shown in FIG. 3A or the alternative surgical drain 130 shown in FIG. 3B. The adhesive 108 may be a medical grade pressure sensitive adhesive (PSA) that is suitable for short-term or removable adhesion or implantation. The second surface 104 may be totally or partially covered by the adhesive 108 which may be a continuous coating, a web, or in discrete sections on the surface 104. For a relatively short (e.g. 1-3 cm) probe length 101, the second surface 104 may be totally covered with the adhesive 108. For a relatively long (e.g. 4-6 cm) probe length 101, only a proximal portion (i.e. closer to a protective jacket 114) of the second surface 104 may be covered with the adhesive 108. For example, only the proximal 1-3 cm of the 4-6 cm long second surface 104 may be covered with the adhesive 108. This partial coverage with the adhesive 108 may be preferred in instances where it is desirable to maintain the bending flexibility of the probe 100 when it is attached to the surgical drain 120.

A protective release liner (not shown) may normally cover the adhesive 108 to prevent unintentional adherence to other surfaces or devices. This release liner may be peeled off or otherwise removed to expose the adhesive 108 just prior to the attachment of the probe 100 to other devices such as the surgical drain 120, for example.

It is understood by one of ordinary skill in the art that alternative embodiments of means for attaching or mounting the probe to another body include hook and loop type fasteners (e.g., Velcro), fastening straps, tapes or other types of fasteners that attach the probe and the other body permanently or releasably.

The probe 100 includes a set of through-openings 112 extending between the first surface 102 and the second surface 104. The openings 112 may be elongated in shape (e.g. rectangular slots) to facilitate and improve aperture coupling to drainage formations such as openings 122 of the surgical drain 120 as shown in FIG. 3A or to drainage formations such as grooves 132 of surgical drain 130 as shown in FIG. 3B. Alternatively, the openings 112 may assume any other shape in their cross-section, including circular, elliptical, square, hexagonal, or rhombic. The relative positions of the openings 112 may be prearranged to match with the relative positions of the openings 122 of the surgical drain 120 on which the probe 100 is to be mounted. Alternatively, the relative positions of the openings 112 may be prearranged to match with the relative positions of the grooves 132 of the surgical drain 130 on which the probe 100 is to be mounted.

Figure 3C:
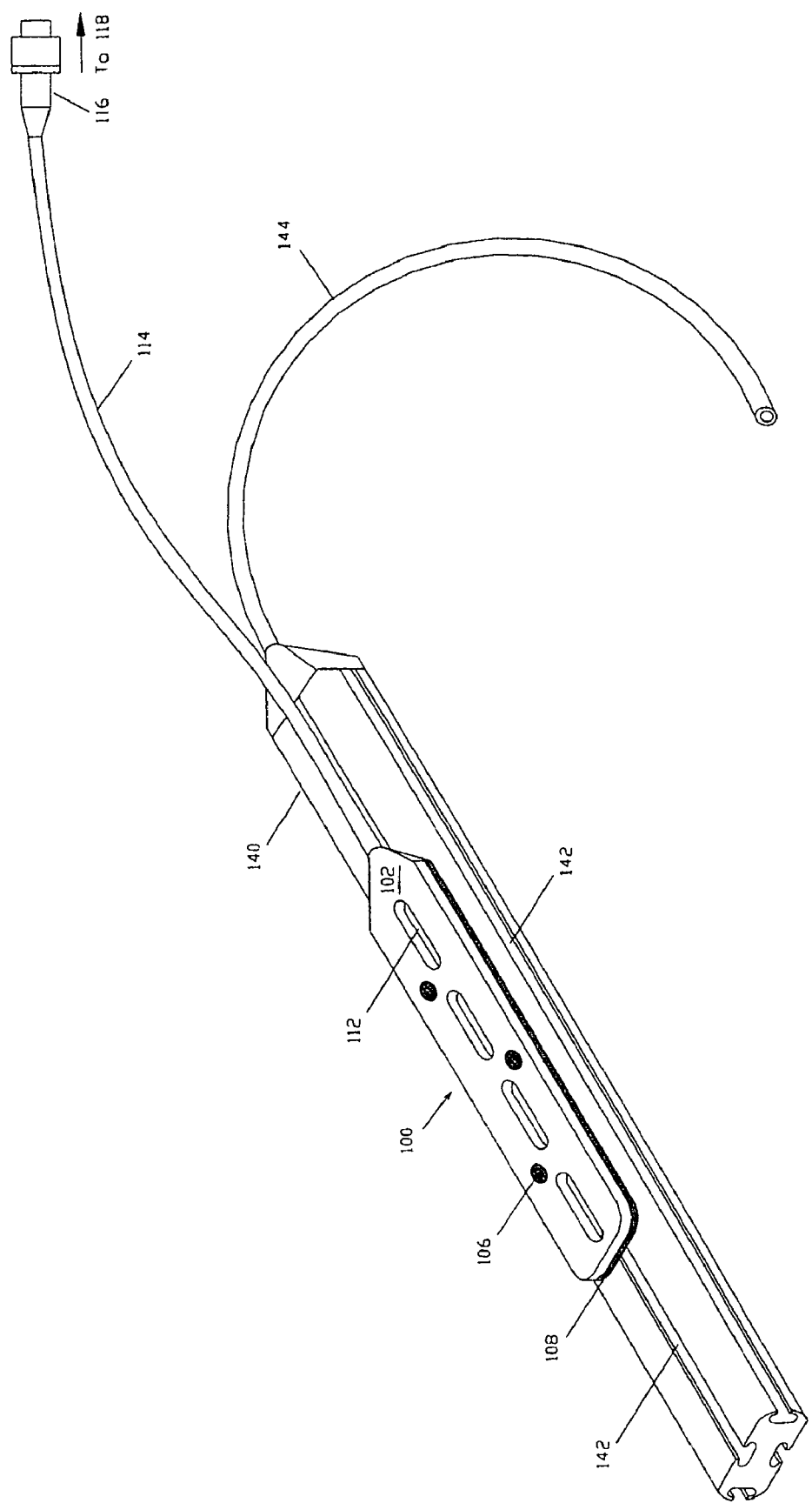
FIG. 3C shows another embodiment of the probe mounted on an alternative surgical drain with draining grooves.
Figure 3D:
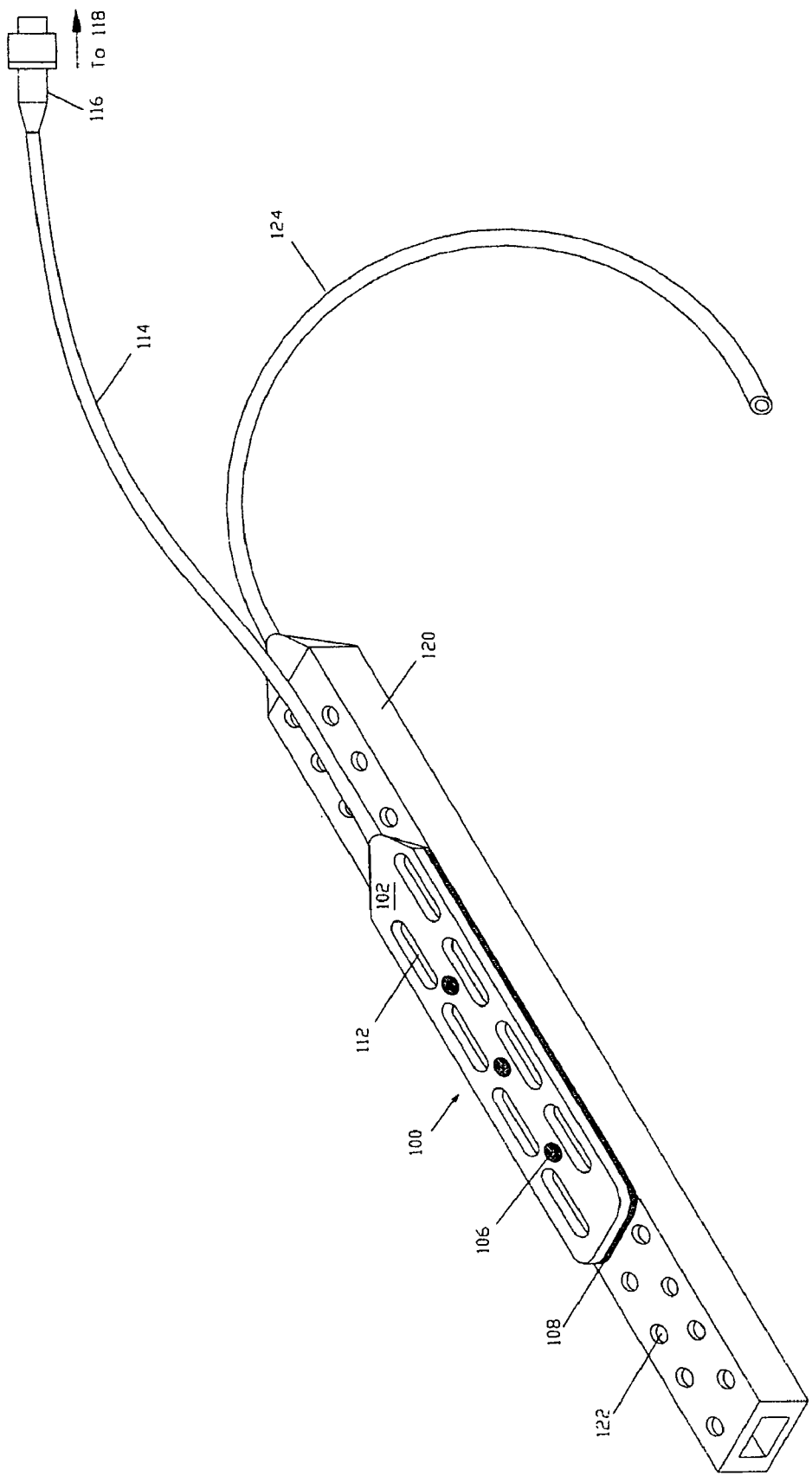
FIG. 3D shows another embodiment of the probe mounted on a surgical drain with draining holes.

The openings may be arranged in a dual or multi-row configuration as shown for example in FIGS. 3A and 3B or in a single-row configuration as shown in FIG. 3C to reflect the drainage configuration of the corresponding surgical drain with which the probe is used. In the dual-row configuration, the openings 112 of the first and second rows may be symmetric about the long axis of the probe as shown for example in FIG. 3B. Alternatively the openings 112 of the first and second rows may be asymmetric about the long axis of the probe as shown for example in FIG. 3D.

In the single row configuration shown in FIG. 3C, the probe 100' having a single-row arrangement of the openings 112 may be attached to a surgical drain 140 with a centered draining groove 142. In this configuration, the sensors 106 may be disposed on either side of the openings 112.

The surgical drains 120, 130 and 140 have draining tubes 124, 134, and 144 respectively extending from a proximal end of the drains. The draining tubes 124, 134, and 144 may be exteriorized out of the body and connected to an external suction device or a drain bulb (reservoir) to suck out and collect the wound fluids.

The sensors 106 of the probe may be preferably of the fiberoptic type, however, they may be of any other type including electronic and hydraulic (e.g. for pressure measurements). Alternatively, the sensors may be a combination of the fiberoptic, electrical and hydraulic types. The cables (e.g. optical fibers, wires and/or tubes) of the sensors 106 may be bundled within a protective jacket 114 and guided from a proximal end of the probe to a connector 116 that connects the probe 100 to a monitoring unit 118 that drives the sensors 106, processes measured data from the sensors, and/or displays physiological parameters obtained from the measured data to the user.

A reinforcement tensile member 110, such as a wire, cable or woven or non-woven fiber, may be embedded within the probe 100 (or 100'), preferably within the perimeter of the probe 100, and extends continuously through the protective jacket 114 between a distal end of the probe and the connector 116 as shown in FIG. 2. In the illustrated embodiment, the member 110 is a single, continuous fiber whose one end extends from the connector 116 and whose other end returns to the connector 116. The reinforcement member 110 may serve to strengthen the structural integrity of the probe 100 (or 100') especially when it is being pulled out of the body along with the surgical drain by, for example, the manual grabbing of both the protective jacket 114 and the draining tubes 124, 134, or 144 of the surgical drains 120, 130 or 140, respectively.

Although the probe 100 may be preferably rectangular in shape with a flat cross-section, it may assume other shapes including a C-shaped cross-section to enable its mounting on and/or attachment to rounded drains with circular cross-sections.

Figure 4A:
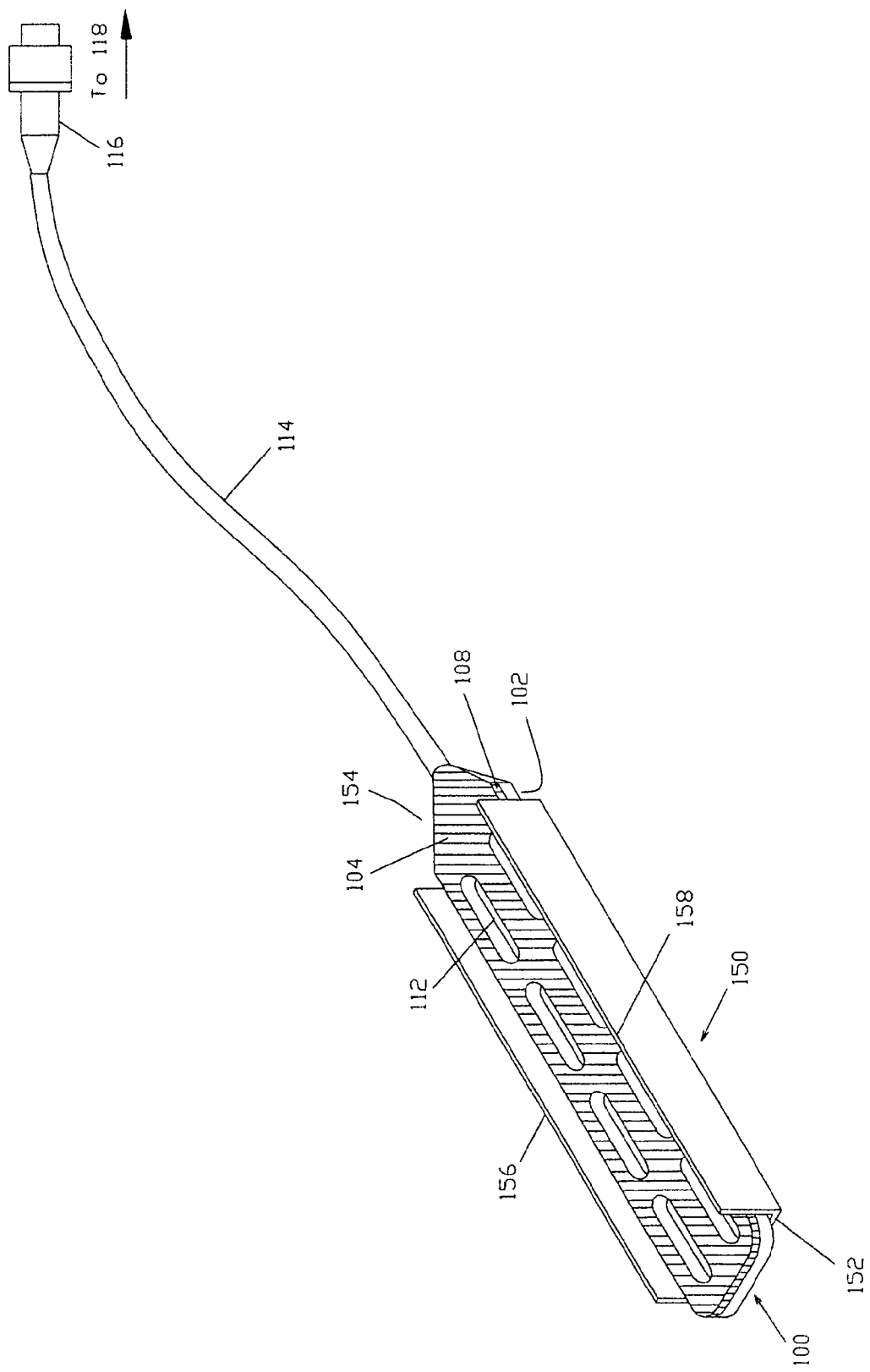
FIG. 4A shows an embodiment of the probe on its applicator.

Prior to its application, the probe 100 may have an applicator 150 to facilitate its handling, calibration, and aligned attachment to the surgical drains. FIG. 4A illustrates an applicator 150 that may be used to attach the probe 100 to a surgical drain of the flat type as shown in FIG. 3. An embodiment of the applicator 150 may be a U-shaped plastic channel or tray member with a bottom 152 and two sides 156, 158 defining an opening 154 therebetween. The probe body 103 is lodged in the applicator 150 as shown in FIG. 4, with its first side 102 facing the bottom 152 of the applicator, and its second side 104 facing the opening 154. The inner surface of the bottom 152 may include a calibration standard (not shown) to allow the calibration of the facing sensors 106 prior to the application of the probe 100. The calibration standard may be an optically reflective material with known reflective characteristics (or spectrum) to be used in calibrating optical sensors of the reflective type. The sides 156 and 158 of the applicator may extend above or beyond the thickness of the probe 100 so the applicator can also receive within its U-shaped channel a surgical drain to which the probe 100 is to be attached. Outer surface of the sides 156 and 158 may have a grip impression (not shown) to facilitate the handling of the applicator 150.

Figure 4B:
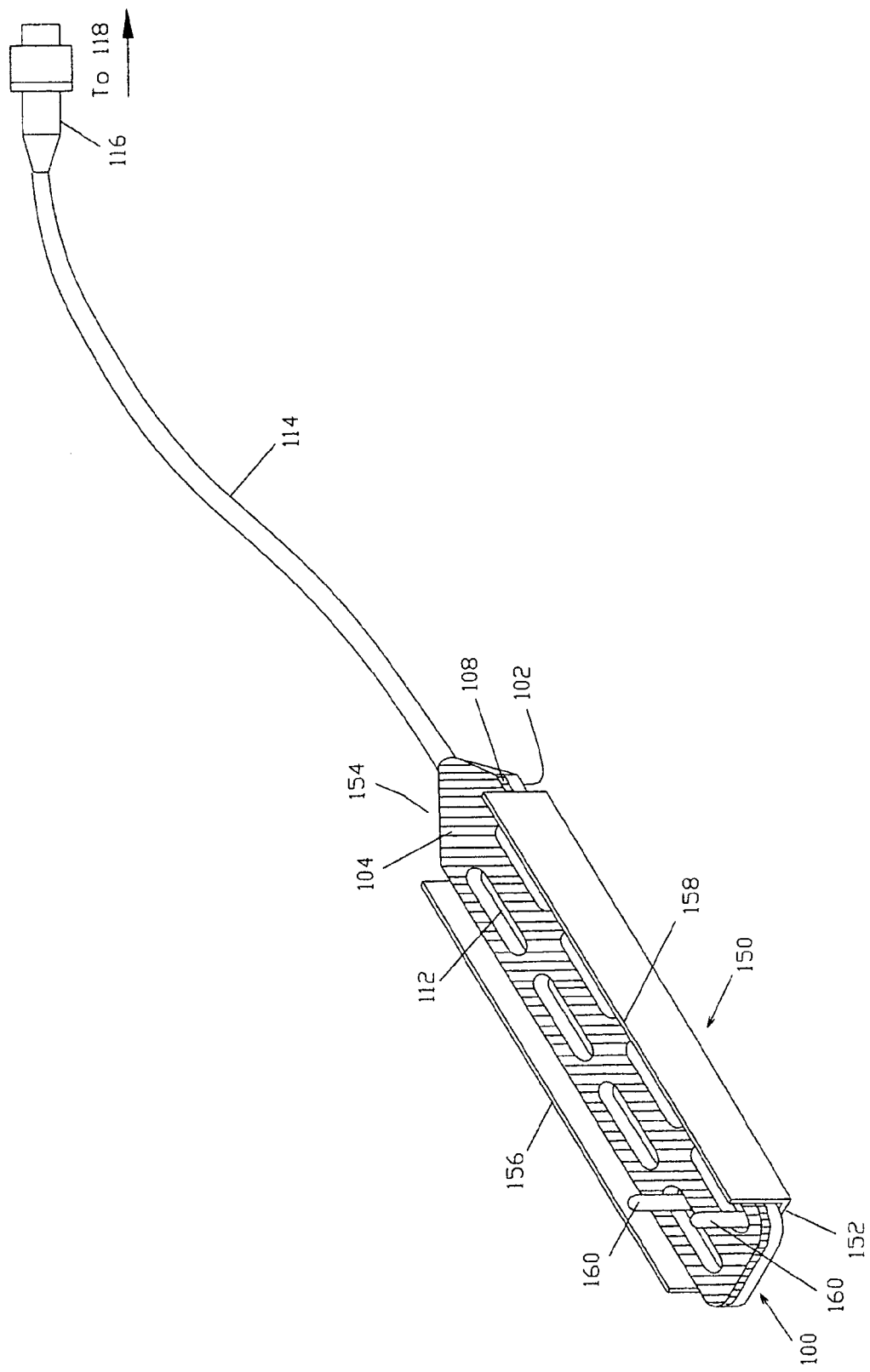
FIG. 4B shows an embodiment of the probe on an applicator having guide pins.

The applicator 150 may also include raised formations, for example, guide protrusions, prongs, nubs, teeth or pins 160, as shown in FIG. 4B extending from the bottom side 152. The guide pins 160 are configured in size and dimension to extend through the openings 112 of the probe 100 to facilitate the alignment of the openings 112 to the openings 122 of the surgical drain 120 (e.g. in the Jackson-Pratt type) as shown in FIG. 3A or to the grooves 132 of the surgical drain 130 (e.g. in the Blake type) as shown in FIG. 3B. In a typical probe attachment procedure, the probe is inserted into the applicator with the first surface 102 facing the bottom 152 of the applicator 150 and the pins 160 extending through the openings 112 of the probe. Any release liner protecting the adhesive 108 on the second surface 104 of the probe facing the opening of the U-shaped channel of the applicator is removed to expose the adhesive 108. The surgical drain 120 or 130 is then inserted into the opening of the U-shaped channel of the applicator to contact the adhesive 108 with the pins 160 also aligned with and inserted into the openings 122 or the grooves 132 of the drain as the applicator 150 holding the probe 100 and the surgical drain are pressed together. Attached to each other by the adhesive 108, a resulting probe and drain assembly is removed from the applicator and ready for use inside a patient's body. The openings 112 are in communication with the openings 122 or grooves 132 of the drain and the sensors 106 remain exposed for monitoring the tissue or organ of interest.

Figure 5:
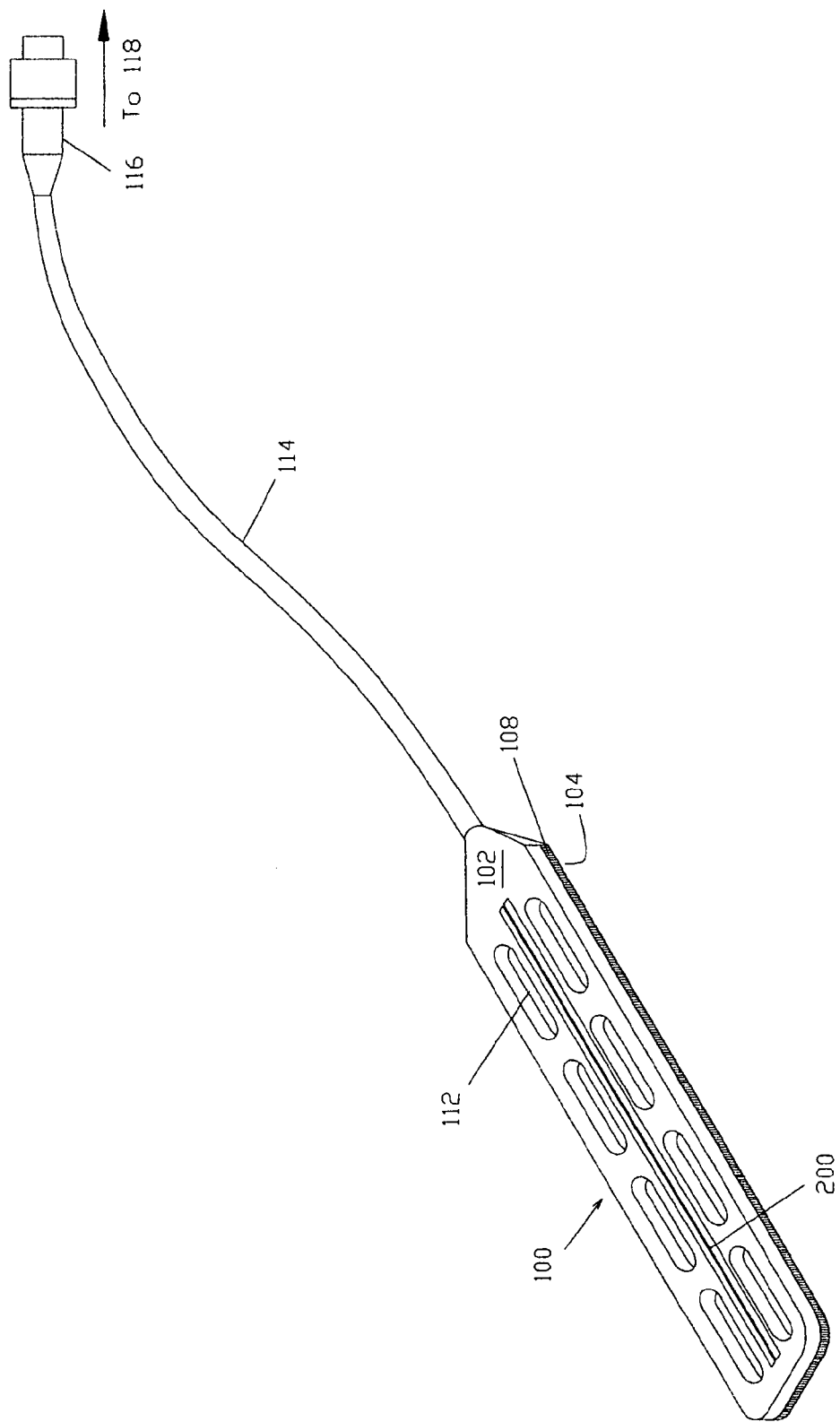
FIG. 5 shows an embodiment of the probe with a line sensor.

The probe 100 may include discrete or unit sensors 106 to measure the physiological parameters of the tissue facing the sensor. Alternatively, the probe 100 may include an elongated or linear sensor 200 as shown in FIG. 5. The sensor 200 may be composed of a plurality of unit or discrete sensors to measure a physiological parameter along the length of the probe 100. This configuration may be valuable in reducing site-dependency of the measurement and provide a more reliable spatially averaged measurement. Site dependency is the variation in the measured value of the physiological parameters depending on the sensor location on the tissue.

An embodiment of an optical reflectance elongated sensor 200 is shown in FIGS. 6A, 6B and 6C. The sensor 200 may be used to measure the spatially averaged optical reflectance characteristics of adjacent tissue 201. The optical reflectance characteristics of the adjacent tissue 201 may be used to determine the percent saturation of tissue hemoglobin (tissue oxygenation), and the concentration of biological material (e.g. bile) and/or exogenous materials (e.g. drugs).

The reflectance sensor 200 is composed of at least one transmit optical communication apparatus, for example, wave guide, hollow optical guide, or optical fiber 202, and at least one receive optical communication apparatus, for example, wave guide, hollow optical guide, or optical fiber 204. Distal end apertures 206 and 208 of the optical fibers 202 and 204 are covered or coated by a reflective material 210 to minimize the loss of light in the fibers from escaping out of the end apertures 206 and 208 by reflecting light back into the fibers 202 and 204, respectively. The optical fibers 202 and 204, preferably of the plastic type, may be fixedly positioned on the probe at a preselected distance 212 (FIG. 6C) from each other.

Sides of the optical fibers 202 and 204 may be slightly indented at multiple equi-distant locations along the length of the fibers spanning the probe to create a series of micro mirrors (or reflectors, used interchangeably herein) 214 and 216, respectively. The micro mirrors 214 and 216 may be cylindrical or convex in shape and are capable of emitting and collecting light at about 90-degrees to the axis of the optical fibers 202 and 204, respectively. The micro mirrors may be thermo mechanically indented into the sides of plastic optical fibers and a cladding material and/or a reflective material may be applied on to the indentation sites.

Light passing through the transmit optical fiber 202 may be reflected by each micro mirror 214 to be emitted as light portion 215 (FIG. 6C) at about 90-degrees to the axis of the fiber 202. Similarly, light portion 217 that is incident at about 90-degrees to the axis of the optical fiber 204 may be reflected by each micro mirror 216 into the optical fiber 204. Therefore, the optical fibers 202 and 204 have a series of corresponding mirrors 214 and 216 that may respectively emit and collect light at about 90-degrees to the axis of the optical fibers 202 and 204, respectively.

An optical isolator 218 may be placed between the optical fibers 202 and 204 spanning the length of the probe to minimize crosstalk or direct light transmission between the two fibers 202 and 204. The optical isolator 218 may be an opaque absorptive wafer. A thin sheet 220 of transparent material such as medical grade transparent silicone may be used to cover the optical fibers 202 and 204 to isolate them from the adjacent tissue 201.

The above elongated sensor 200 may be embedded in the probe 100 as shown in FIG. 5. In a typical application, with proximal portions of the fibers 202 and 204 extending through the protective jacket 114 between the probe and the monitoring unit 118, a light source (not shown) in the monitoring unit 118 may transmit light into the transmit optical fiber 202 where it may be side-emitted as a light portion 215 by the mirrors 214 into the tissue 201 (FIG. 6C) adjacent to the first surface 102 of the probe 100. The tissue 201 reflects some of the emitted light portion 215 back to the sensor 200 where it may be collected as light portion 217 by the mirrors 216 and channeled into the receive optical fiber 204. The receive optical fiber 204 guides the reflected light to a spectrometer (not shown) in the monitoring unit 118 to measure its spectral characteristics. The spectral characteristics may be processed by a processor (not shown) in the monitoring unit 118 to obtain the value of the desired physiological parameters such as, for example, the percent oxygen saturation of the tissue. One advantage of using the sensor 200 is that it may allow the optical interrogation of an elongated segment of the tissue 201 rather than just a single location. This tends to decrease the site-dependency of the measurement and improve the reliability of the measured physiological parameters.

Alternative to the mounting of the probe to a surgical drain, the probe may be attached to a wound dressing with the adhesive layer facing the wound dressing and the sensors facing the tissue to be monitored. This configuration may be beneficial in monitoring superficial tissue grafts (e.g. skin) and burn wounds. For such application, the through-openings of the probe may be a network of holes that couples to the wound dressing and allow the absorption of tissue exudate into the fibers of the dressing. The method of application may include attaching the probe to the wound dressing, both placed on the tissue to be monitored, and the wound exudate seeping through the openings of the probe to be absorbed by the wound dressing.

Although the above detailed description describes and illustrates various preferred embodiments, the invention is not so limited. Many modifications and variations will now occur to persons skilled in the art. As such, the preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A system for monitoring tissue:
   a probe with through openings;
   a surgical drain with drainage formations;
   an applicator for applying the probe to the surgical drain wherein the applicator is configured to align at least one of the openings of the probe with a drainage formation to establish fluid communication; and means for attaching the probe to the surgical drain;
   wherein the applicator has formations received in the openings to facilitate alignment.

2. A system of claim 1, wherein the means for attaching is a pressure sensitive adhesive between the probe and the surgical drain.

3. A system of claim 1, wherein the drainage formations of the surgical drain are drainage openings.

4. A system of claim 1, wherein the drainage formations of the surgical drain are drainage grooves.

5. A system for monitoring tissue:
   a probe with through openings;
   a surgical drain with drainage formations;
   an applicator for applying the probe to the surgical drain wherein the applicator is adapted to align at least one of the openings of the probe with a drainage formation to establish fluid communication; and means for attaching the probe to the surgical drain;
   wherein the applicator has a U-shaped configuration configured to receive the probe and the surgical drain.

6. A system of claim 5, wherein the means for attaching is a pressure sensitive adhesive between the probe and the surgical drain.

7. A system of claim 5, wherein the drainage formations of the surgical drain are drainage openings.

8. A system of claim 5, wherein the drainage formations of the surgical drain are drainage grooves.

9. A system for monitoring tissue:
   a probe with through openings;
   a surgical drain with drainage formations;
   an applicator for applying the probe to the surgical drain wherein the applicator is configured to align at least one of the openings of the probe with a drainage formation to establish fluid communication; and means for attaching the probe to the surgical drain;
   wherein the applicator has pins that extend into the openings configured to facilitate alignment.

10. A system of claim 9, wherein the means for attaching is a pressure sensitive adhesive between the probe and the surgical drain.

11. A system of claim 9, wherein the drainage formations of the surgical drain are drainage openings.

12. A system of claim 9, wherein the drainage formations of the surgical drain are drainage grooves.

* * * * *